(12) United States Patent
Salnik et al.

(10) Patent No.: US 7,403,022 B2
(45) Date of Patent: Jul. 22, 2008

(54) METHOD FOR MEASURING PEAK CARRIER CONCENTRATION IN ULTRA-SHALLOW JUNCTIONS

(75) Inventors: Alex Salnik, Castro Valley, CA (US); Lena Nicolaides, Castro Valley, CA (US); Jon Opsal, Livermore, CA (US); Mira Bakshi, Hayward, CA (US)

(73) Assignee: KLA-Tencor, Inc., Milpitas, CA (US)

( * ) Notice: Subject to any disclaimer, the term of this patent is extended or adjusted under 35 U.S.C. 154(b) by 371 days.

(21) Appl. No.: 11/334,962

(22) Filed: Jan. 19, 2006

(65) Prior Publication Data

US 2006/0166385 A1    Jul. 27, 2006

Related U.S. Application Data

(60) Provisional application No. 60/645,627, filed on Jan. 21, 2005.

(51) Int. Cl.
   *G01R 31/02* (2006.01)
(52) U.S. Cl. ..................... 324/751
(58) Field of Classification Search ........ 324/751, 324/765, 760, 158.1, 766, 719, 724, 252; 250/372; 438/16, 17, 18, 7; 356/455, 432
   See application file for complete search history.

(56) References Cited

U.S. PATENT DOCUMENTS

| | | | |
|---|---|---|---|
| 4,634,290 A | 1/1987 | Rosencwaig et al. ......... 374/5 |
| 4,646,088 A | 2/1987 | Inoue ................. 340/870.31 |
| 4,854,710 A | 8/1989 | Opsal et al. .................. 356/432 |
| 5,074,699 A | 12/1991 | Blaisdell et al. ............. 403/122 |
| 5,854,719 A | 12/1998 | Ginosar et al. ................. 360/69 |
| 5,978,074 A | 11/1999 | Opsal et al. .................... 356/72 |
| 6,452,685 B2 | 9/2002 | Opsal et al. .................. 356/601 |
| 6,532,070 B1* | 3/2003 | Hovinen et al. ............. 356/369 |
| 6,888,632 B2* | 5/2005 | Smith ......................... 356/369 |
| 2004/0251927 A1 | 12/2004 | Salnik et al. ................. 324/765 |
| 2004/0253751 A1 | 12/2004 | Salnik et al. .................. 438/16 |
| 2005/0083528 A1 | 4/2005 | Salnik et al. ................. 356/445 |

OTHER PUBLICATIONS

L. Nicolaides et al., "Nondestructive analysis of ultrashallow junctions using thermal wave technology," *Review of Scientific Instruments*, vol. 74, No. 1, Jan. 2003, pp. 586-588.

A. Salnik et al., "Simultaneous determination of ultra-shallow junction depth and abruptness using thermal wave technique," *Review of Scientific Instruments*, vol. 75, No. 6, Jun. 2004, pp. 2144-2148.

* cited by examiner

*Primary Examiner*—Ha Nguyen
*Assistant Examiner*—Tung X Nguyen
(74) *Attorney, Agent, or Firm*—Stallman & Pollock LLP (57) ABSTRACT

A method is disclosed for determining peak carrier concentration in ultra shallow junctions of semiconductor samples. A region of the surface of the sample is periodically excited. The effects of the excitation are monitored by a probe beam. Synchronous detection produces in-phase (I) and quadrature (Q) signals. These signals are compared to signals obtained from calibration samples to evaluate peak carrier concentration.

9 Claims, 8 Drawing Sheets

METHOD FOR MEASURING PEAK CARRIER CONCENTRATION IN ULTRA-SHALLOW JUNCTIONS

PRIORITY

This application claims priority from U.S. Provisional Application Ser. No. 60/645,627, filed Jan. 21, 2005.

TECHNICAL FIELD

The subject invention relates to optical devices used to non-destructively evaluate semiconductor wafers. In particular, the present invention relates to systems for measuring carrier concentration in semiconductor samples.

BACKGROUND OF THE INVENTION

As geometries continue to shrink, manufacturers have increasingly turned to optical techniques to perform non-destructive inspection and analysis of semiconductor wafers. The basis for these techniques is the notion that a sample may be examined by analyzing the reflected energy that results when an optical beam is directed at a sample. This type of inspection and analysis is known as optical metrology and is performed using a range of different optical techniques.

One widely used type of optical metrology system includes a pump laser. The pump laser is switched on and off to create an intensity-modulated pump beam. The pump beam is projected against the surface of a sample causing localized periodic excitation of the sample. As the pump laser is modulated, the localized periodic excitation creates a train of thermal and plasma waves within the sample. These waves reflect and scatter off various features and interact with various regions within the sample in a way that alters the flow of heat and/or plasma from the pump beam spot.

The presence of the thermal and plasma waves has a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be investigated.

To monitor the surface changes, a probe beam is directed at a portion of the sample that is illuminated by the pump laser. A photodetector records the intensity of the reflected probe beam. The output signal from the photodetector is filtered to isolate the changes that are synchronous with the pump beam modulation. For most implementations, this is performed using a heterodyne or lock-in detector (See U.S. Pat. No. 5,978,074 and in particular FIG. 2 for a discussion of such a lock-in amplifier/detector). Devices of this type typically generate separate "in-phase" (I) and "quadrature" (Q) outputs. These outputs are then used to calculate amplitude and phase of the modulated signal using the following equations:

$$\text{Amplitude} = \sqrt{I^2 + Q^2} \quad (1)$$

$$\text{Phase} = \arctan(Q/I) \quad (2)$$

Figure 1:
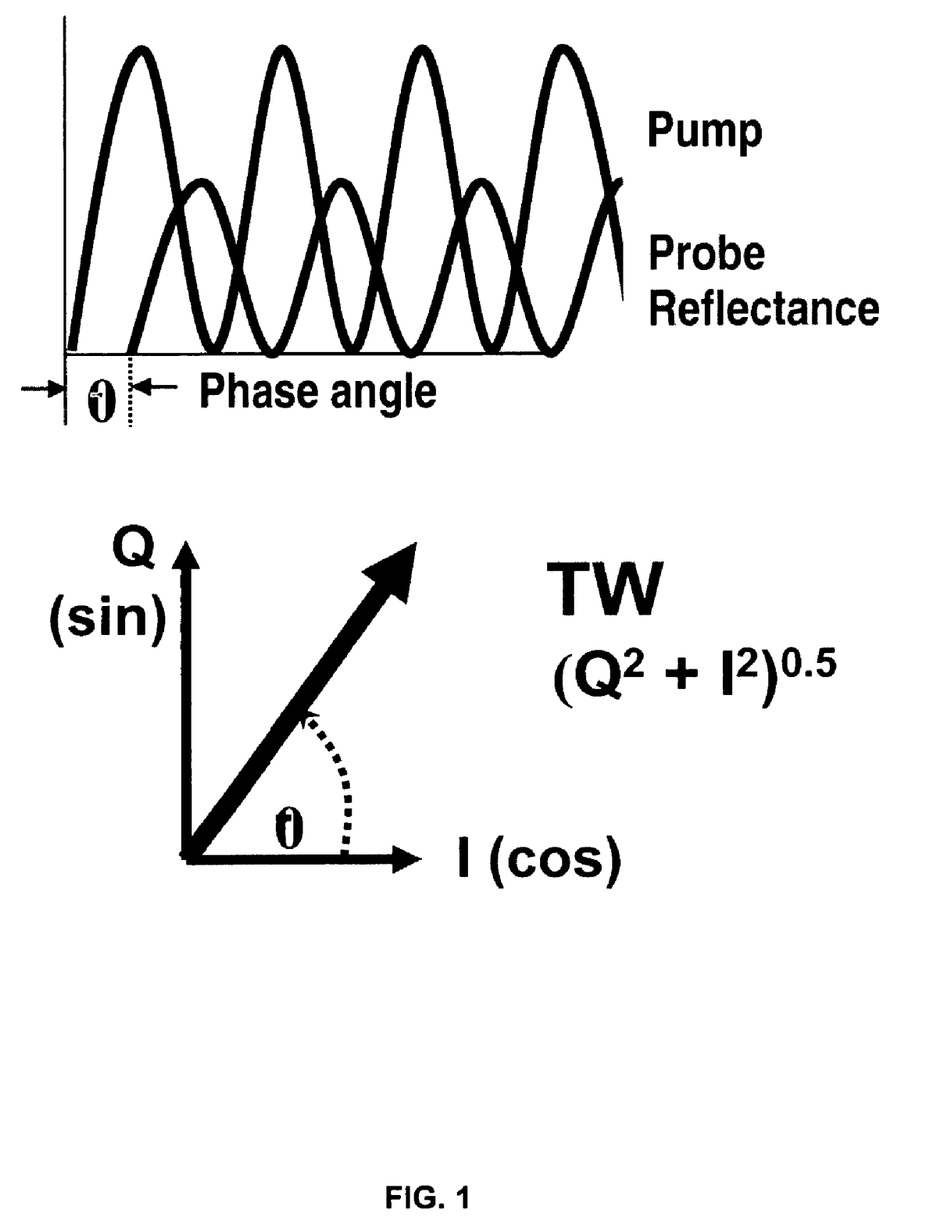
FIG. 1 is an illustration of the in-phase (I) and quadrature (Q) components which can be derived from the synchronous detection of a pump and probe beam device.

The origin of the phase angle and the geometry of "in-phase" and "quadrature" components are illustrated in FIG. 1.

The amplitude and phase values are used to deduce physical characteristics of the sample. In most cases, this is done by measuring amplitude values (amplitude is used more commonly than phase) for one or more specially prepared calibration samples, each of which has known physical characteristics. The empirically derived values are used to associate known physical characteristics with corresponding amplitude values. Amplitude values obtained for unknown samples can then be analyzed by comparison to the amplitude values obtained for the calibration samples.

Systems of this type (i.e., those using external means to induce thermal or plasma waves in the sample under study) are generally referred to as PMR (photomodulated reflectance) type systems. PMR-type systems are used to study a range of attributes, including material composition and layer thickness. PMR-type systems and their associated uses are described in more detail in U.S. Pat. Nos. 4,634,290, 4,646,088, 4,679,946; 4,854,710, 5,854,719, 5,978,074, 5,074,699 and 6,452,685. Each of these patents is incorporated in this document by reference.

One PMR-type system is manufactured and sold by the assignee herein under the name Therma-Probe and is discussed below with respect to FIG. 8.

Another important use of PMR-type systems is measurement and analysis of the dopants added to semiconductor wafers before and after their activation. Dopants are ions that are implanted to semiconductors during a process known as ion implantation. The duration of the ion implantation process (i.e., total exposure of the semiconductor wafer) controls the resulting dopant concentration. The ion energy used during the implantation process controls the depth of implant. Both concentration and depth are critical factors that determine the overall effectiveness of the ion implantation process.

PMR-type systems are typically used to inspect wafers at the completion of the ion implantation process. The ion implantation damages the crystal lattice as incoming ions come to rest. This damage is typically proportional to the concentration and depth of ions within the crystal lattice. This makes measurement of damage an effective surrogate for direct measurement of dopant concentration and depth.

For this purpose, a PMR-type optical metrology tool with advanced signal processing algorithms is used to record both quadrature (Q) and in-phase (I) components of the signal for a series of specially prepared calibration samples. The measurement method then performs a linear fit using the recorded points to define a calibration line within an I-Q plane. The slope of this line is defined by the implantation energy and the points along the line correspond to different dopant concentrations. Thus, the damage profile can be characterized by comparison of measured and calibration data in I-Q space. Characterization of samples using I and Q outputs is described in U.S. Patent Publication No. 2005/0083528, published Apr. 21, 2005, assigned to the same assignee and incorporated here by reference.

Dopant activation after the ion implantation step is usually performed by rapidly heating and cooling the sample is a special chamber. This process is also known as annealing of semiconductor wafers. During the anneal dopant ions diffuse away from the surface and form a concentration profile within the sample. The transition between the implanted region containing activated dopants and the non-implanted substrate is commonly referred to as a junction. For advanced semiconductor manufacturing, it is generally desirable for the implanted and activated region to be shallow, typically 500 Å or less. Devices of this type are generally referred to as having ultra-shallow junctions or USJ.

Figure 2:
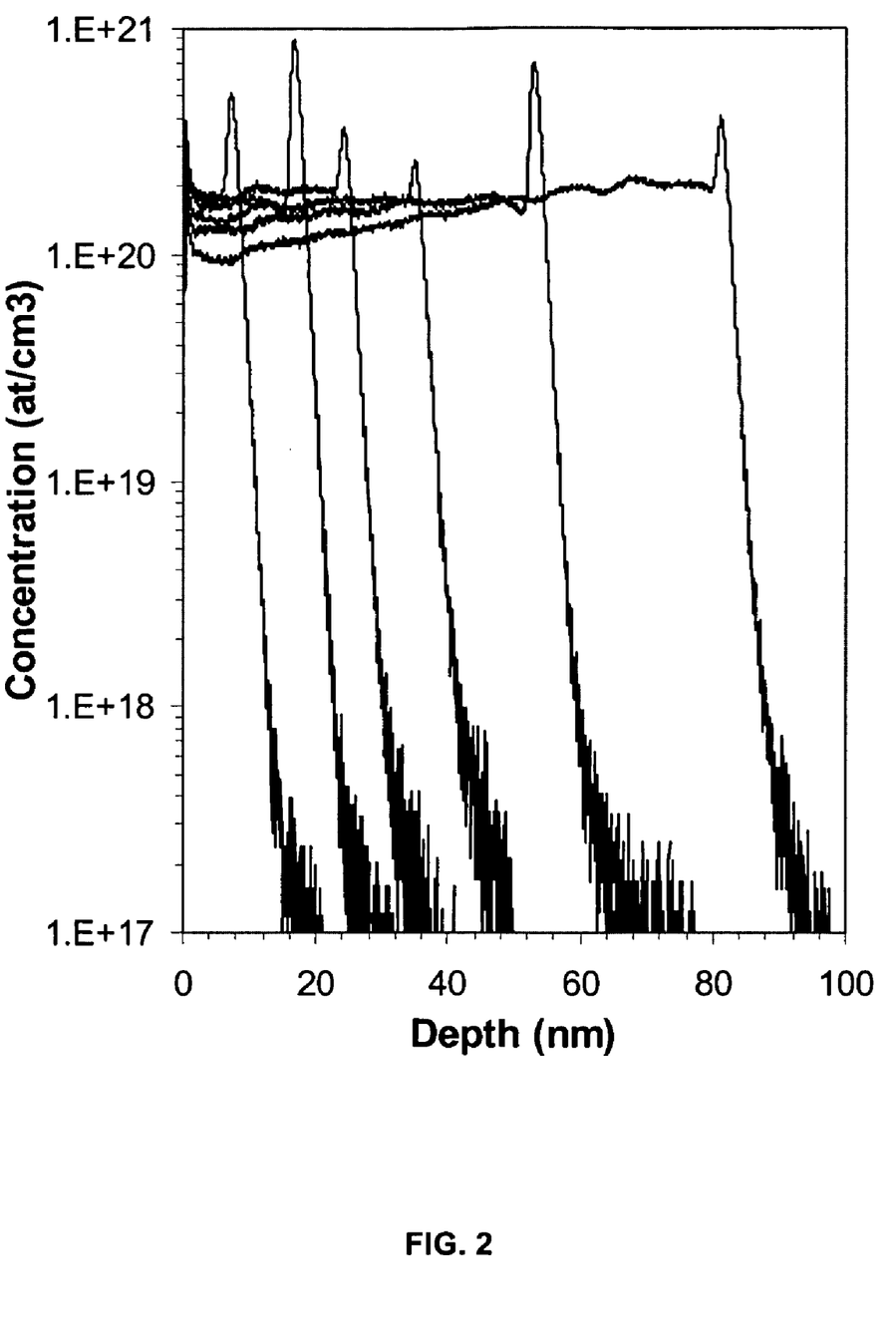
FIG. 2 is a plot of USJ profiles obtained using a secondary ion mass spectroscopy (SIMS) device comparing carrier concentration versus depth below the surface.

A selection of experimentally obtained USJ profiles of six different wafers using secondary ion mass spectroscopy (SIMS) is shown in FIG. 2. We investigated whether it would be possible to characterize an unknown USJ profile (having precisely two unknown characteristics, i.e., junction depth and active dopant level) from a single PMR measurement, involving two independent measurement parameters, i.e., I and Q (or amplitude and phase).

Figure 3:
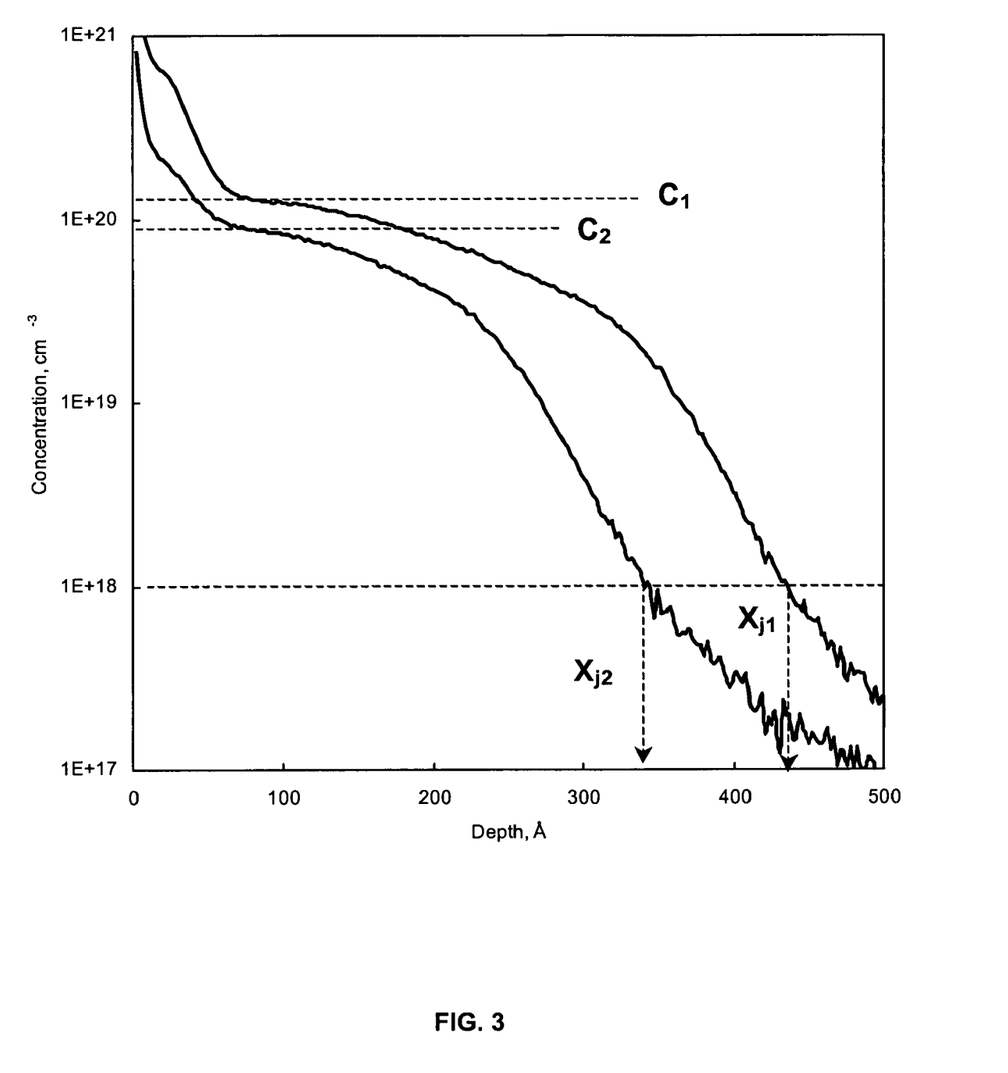
FIG. 3 is a plot of two USJ profiles comparing carrier concentration versus depth.

FIG. 3 illustrates schematically two typical USJ profiles having different peak concentration values ($C_1$ and $C_2$, lying on the upper and lower curves respectively). The quality of USJ wafers is usually assessed using three parameters: junction depth ($X_j$ in FIG. 3), peak carrier concentration (C) and junction abruptness (not depicted in FIG. 3). In practice, the required junction depth is often relatively easy for the manufacturer to achieve. However, keeping the USJ profile abrupt and close to the surface with desired carrier concentration is a big challenge. As a result, techniques to measure $X_j$, C, and abruptness are critical for the manufacture of USJ semiconductors.

A number of techniques have been developed to characterize the effectiveness of USJ process. Destructive and contact methods include secondary ion mass spectroscopy (SIMS), transmission electron microscopy (TEM), and spreading resistance depth profiling (SRP). These techniques are capable of providing detailed USJ profile information, but at the expense of a turnaround time that is usually measured in days or even weeks or at the expense of damaging the surface with contacts.

U.S. Patent Publication No. 2004/0251927, published Dec. 16, 2004, assigned to the same assignee and incorporated herein by reference describes a non-destructive PMR-type system for simultaneous measurements of $X_j$ and abruptness. System of this type performs a series of measurements at different separations between the pump and probe beams followed by the analysis of measured data in I-Q space. A similar approach to measuring USJ depth and abruptness is described in the following publications: L. Nicolaides et al., Rev. Sci. Instrum. 74(1), 586 (2003) and A. Salnick et al., Rev. Sci. Instrum. 75(6), 2144 (2004) incorporated here by reference. See also U.S. Patent Publication No. 2005/0253751, published Dec. 16, 2004, incorporated herein by reference.

While USJ depth and abruptness can be characterized using this method in the above cited patent application, no reliable non-contact and non-destructive technique has been described to monitor the peak carrier concentration in USJ samples.

DETAILED DESCRIPTION OF THE PREFERRED EMBODIMENT

The present invention provides a method for simultaneously monitoring the carrier concentration C and (if desirable) USJ junction depth $X_j$ in non-destructive and non-contact manner. For this method, a PMR-like optical metrology tool is used on USJ samples in a manner similar to that described in U.S. Patent Publication No. 2005/0083528, cited above. In the latter case, I-Q representation of the measurements are used to monitor implant dose, damage and depth. Here we use similar information to derive carrier concentration.

Figure 4:
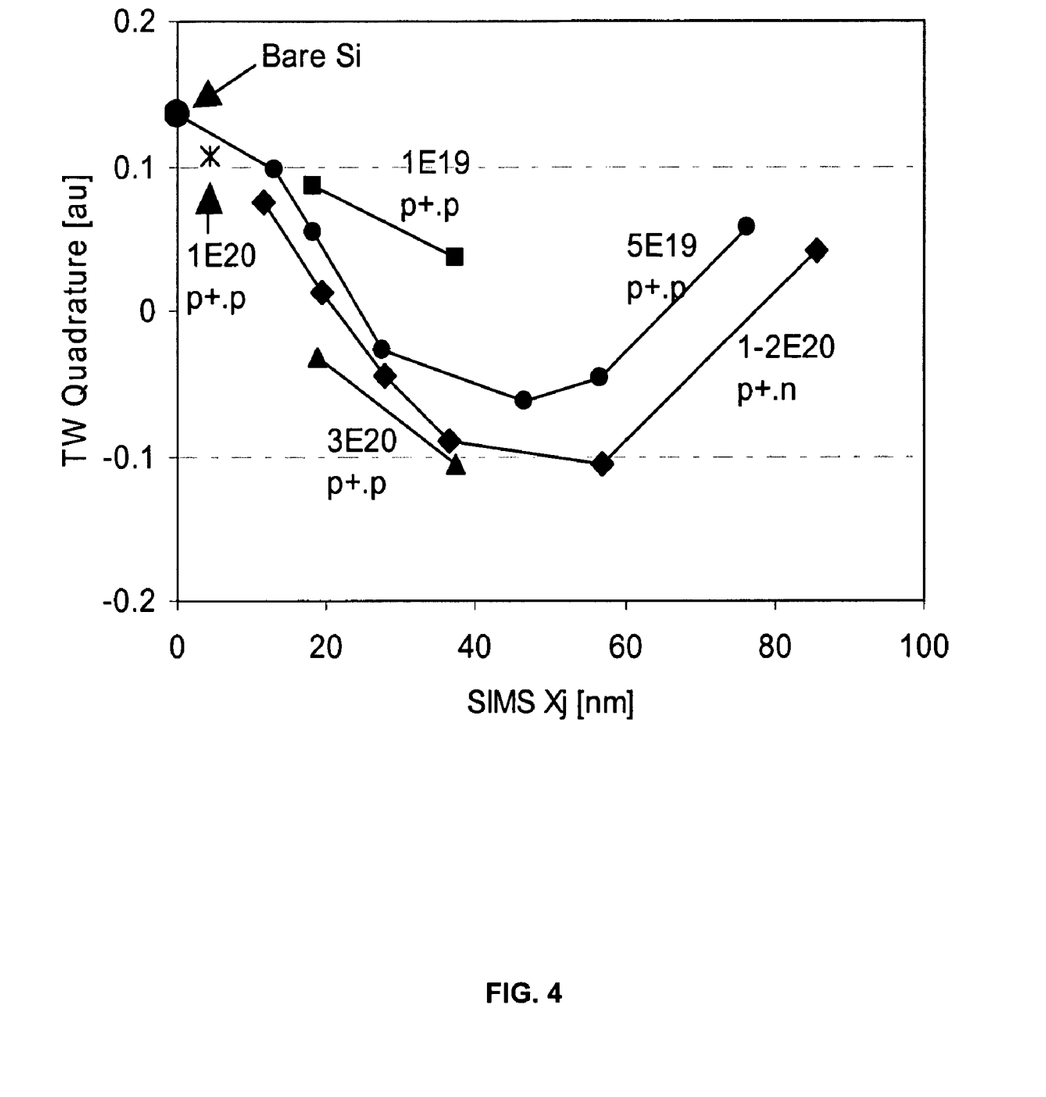
FIG. 4 is a plot of data showing the variation in the TW quadrature signal as a function of depth for a number of different implant samples.

The behavior of the quadrature component of the TW signal for different USJ junction depths and peak carrier levels is illustrated in FIG. 4. As can be seen in FIG. 4, these data sets display the expected cosine-like junction depth dependence for fixed dopant level, with a zero value at approximately 24 nm junction depth. Further, it can be seen that the cosine correlation curve for the more highly doped data series is shifted downwards. Other data we have investigated corresponding to lower and higher dopant values confirm the systematic trend of a Q signal component decrease for higher dopant levels irrespective of the involved junction depth.

FIG. 4 also demonstrates that as the USJ layer thickness converges towards zero, the corresponding quadrature component converges towards the value as measured on a plain, homogeneous, low doped substrate, irrespective of the USJ peak dopant level.

Given the experimental Q signal resolution of $10^{-6}$, this leads to a sub-Angstrom depth resolution in the steeper part of the cosine curve, i.e., near 20 nm where contemporary junctions are located. For a fixed non-zero junction depth, for example 20-30 nm, this leads to a peak carrier concentration sensitivity of better than $10^{18}$ atoms/cm$^3$.

Figure 5:
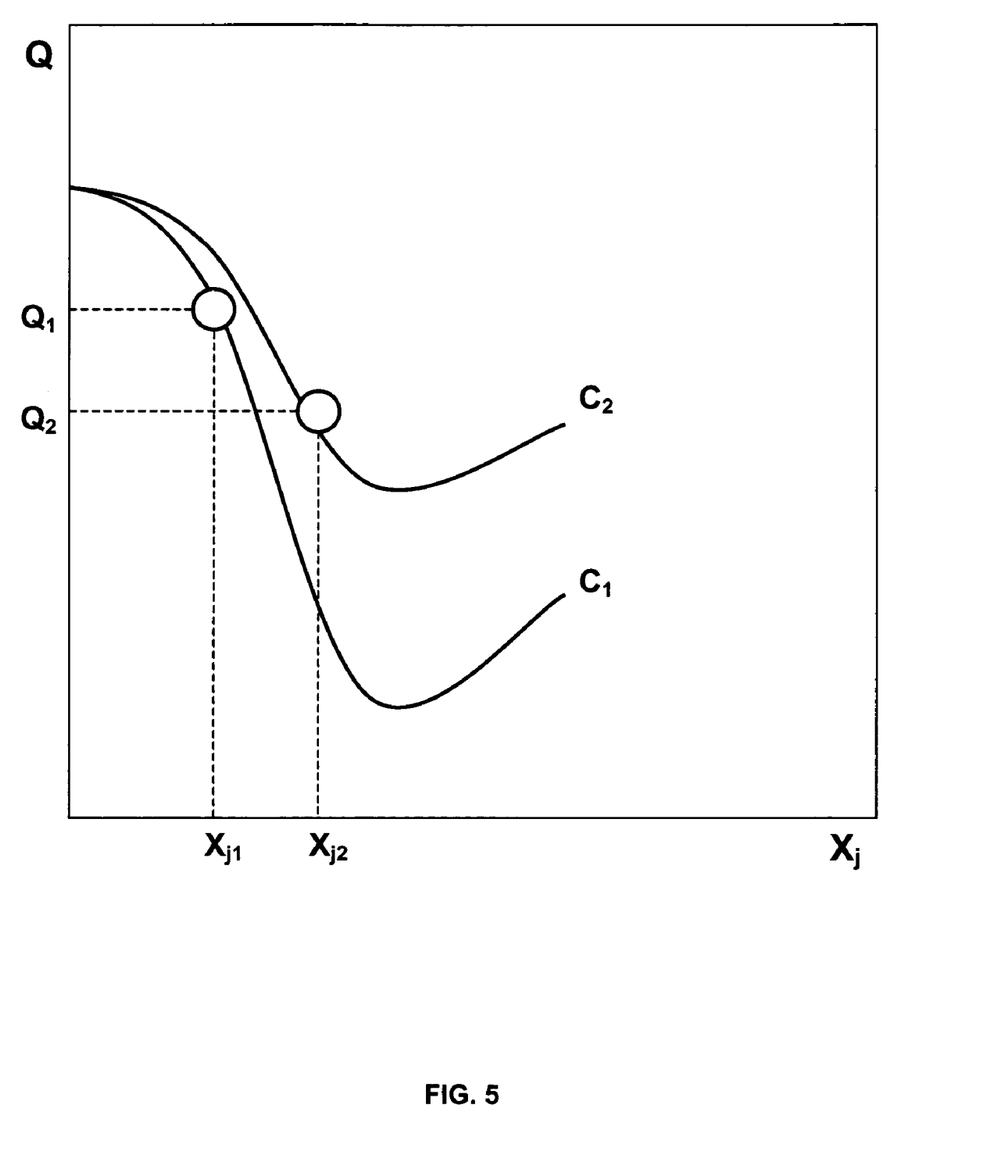
FIG. 5 is a simplified plot showing the variation in the TW quadrature signal as a function of depth.

FIG. 5 shows schematically a simplified basic result of the measurements discussed above. First, different peak carrier concentrations have different depths in a Q vs. USJ depth plot ($C_1 > C_2$ in FIG. 5). Second, each pair of peak concentration and depth ($X_j$) values has its unique corresponding quadrature value. In FIG. 5, a pair $C_1$-$X_{j1}$ corresponds to a quadrature signal component $Q_1$ while $C_1$-$X_{j1}$ pair corresponds to a different value $Q_2$.

To further understand this behavior, PMR theory was used to extract the experimental response. Based on initial work on the thermal and plasma wave technology we developed an advanced tool for simulating the Therma-Probe signal for different types of structures. These simulations take into account, among others, optical parameters such as refractive indices and extinction coefficient for the different wavelengths involved, thermal parameters such as specific heat, thermal conductivity and refractive index (and extinction coefficient) dependence on temperature, and finally plasma parameters such as carrier diffusion coefficient, carrier lifetime and refractive index (and extinction coefficient) dependence on plasma density.

Figure 6:
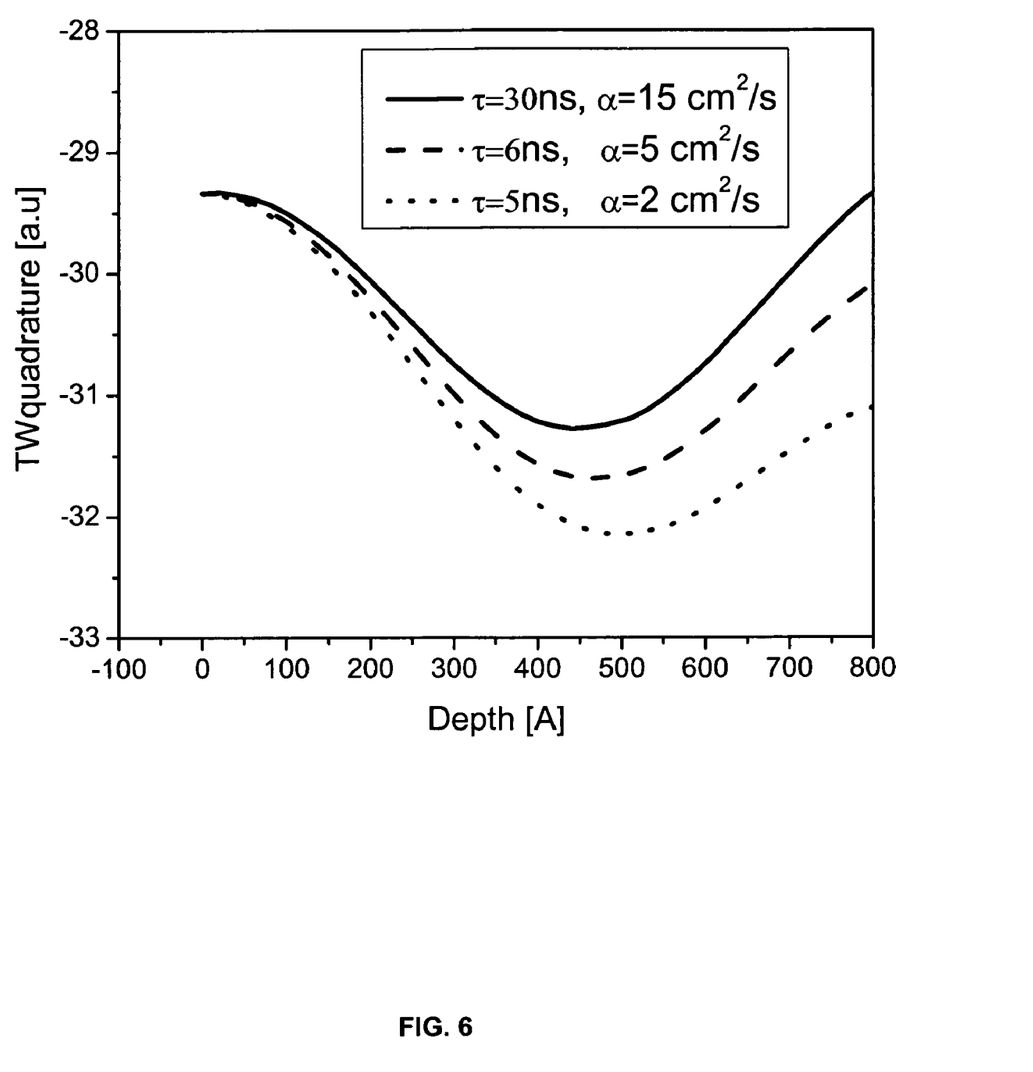
FIG. 6 is a plot of simulations comparing the TW quadrature signal as a function of depth for different carrier lifetimes.

The simulations presented here have been performed for a two-layer system, i.e., a USJ layer and a substrate. Each layer is characterized among others by its recombination rate (i.e., carrier lifetime, $\tau$) and carrier diffusion coefficient ($\alpha$), which is related with the mobility. Both the junction depth and the peak carrier levels have been varied. The latter enters indirectly into the simulations through a faster recombination rate and lower diffusion constant (lower mobility) for higher dopant levels. The results of the simulations are illustrated in FIG. 6. It follows that these simulations are in good qualitative agreement with the experimental data. They correctly predict the lowering of the cosine correlation curve for higher dopant values and the convergence of all curves towards zero depth.

As discussed above, a proprietary method of quadrature and in-phase signals representation has been used in the past as a method of decoupling effects that are not possible by just using the TW signal amplitude. Here, we use a similar approach to obtain carrier concentration of an annealed ultra shallow junction.

Figure 7:
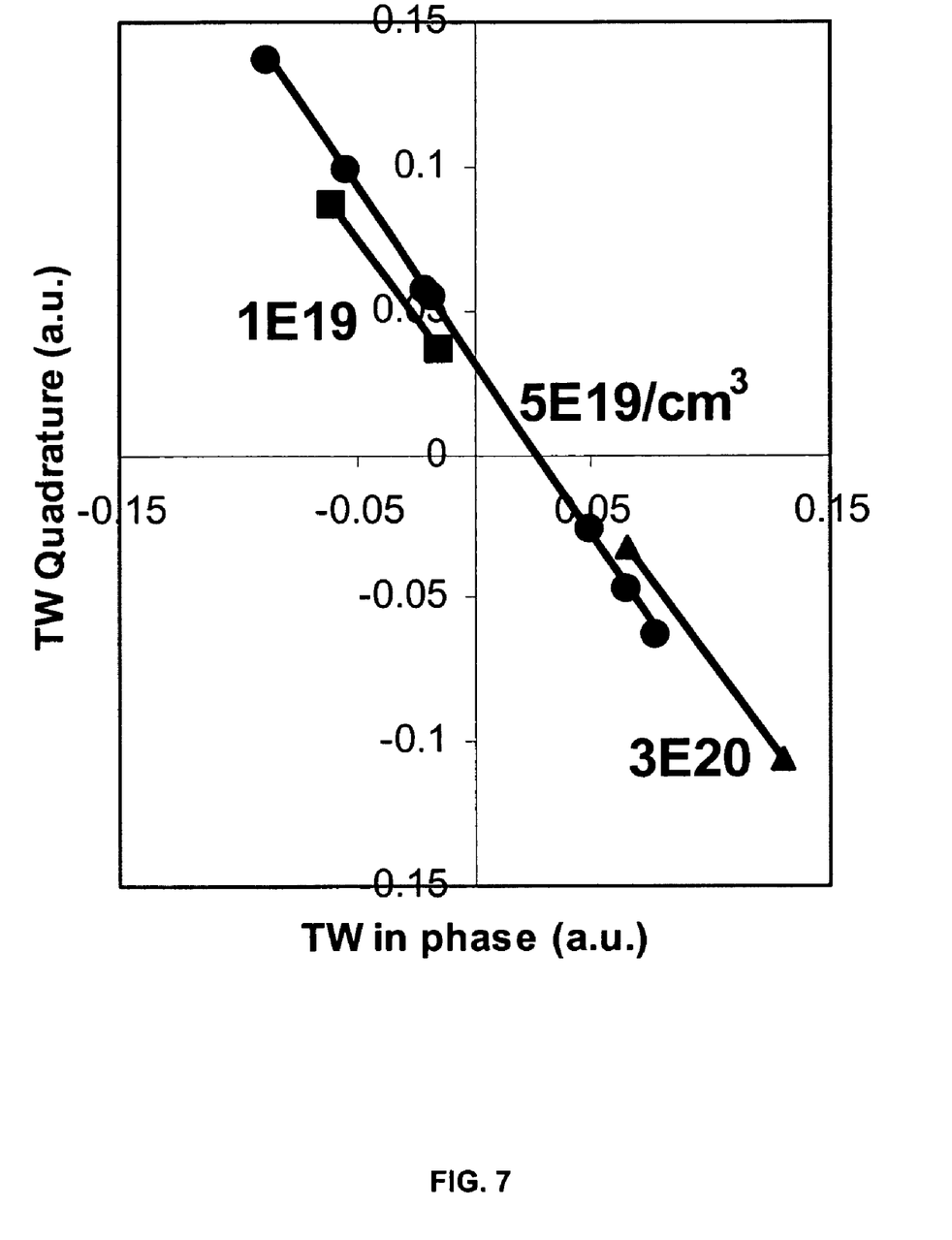
FIG. 7 is a plot of the Q and I values for a number of different calibration wafers.

FIG. 7 illustrates a plot of the in phase versus quadrature components for some of the USJ layers taken with different depths and carrier concentrations. These plots are obtained from calibration wafers which are measured both by a Therma-Probe type device and a secondary ion mass spectroscopy system. The Therma-Probe measurements give the I and Q signals which are then correlated with the carrier concentration and USJ depth information obtained with the SIMS.

The plot of FIG. 7 is interesting in that all the data points for a fixed peak carrier concentration lie on the same straight line. The respective marker positions along such a reference line relate sequentially with the junction depth range going from zero up to a value of 48 nm as one moves from the top left towards the bottom right part of the linear curve. For depths larger than 48 nm one would move back upward the same straight line in agreement with the cosine behavior discussed earlier. Hence, in order to guarantee a unique solution one must limit oneself to measuring junction depths to a level less than 48 nm. Higher or lower peak carrier levels correspond to correlation lines, which lie respectively further away or closer to the origin.

Based on FIG. 7, it can be seen that one can extract independently and uniquely the peak carrier concentration level and junction depth for any unknown USJ structure provided a set of calibration curves as the ones shown in FIG. 7 are available. Indeed, the unique pair of Q-I values measured for the unknown USJ layer will lie, for example, on a single unique specific Q-I correlation curve as shown in FIG. 7, hence, leading automatically to a unique peak carrier concentration level. Furthermore, the same Q-I data pair will have also a unique relative position on that specific selected correlation curve, allowing the immediate read-out of the corresponding junction depth.

Note that if only information about carrier concentration is desired, only two calibration wafers (with different junction depths) for each carrier concentration would be needed. Two calibration wafers would a define unique line for each carrier concentration and any test wafer would fall along one of the lines if it had the same concentration. In practice, it is expected that multiple calibration wafers would be measured so that both carrier concentration and junction depth could be plotted and determined.

In principle would also be possible to derive in a non-destructive way other crucial technological parameters from the same measurement on any unknown USJ layer, such as sheet resistance provided one has information regarding the mobility of the carriers.

Figure 8:
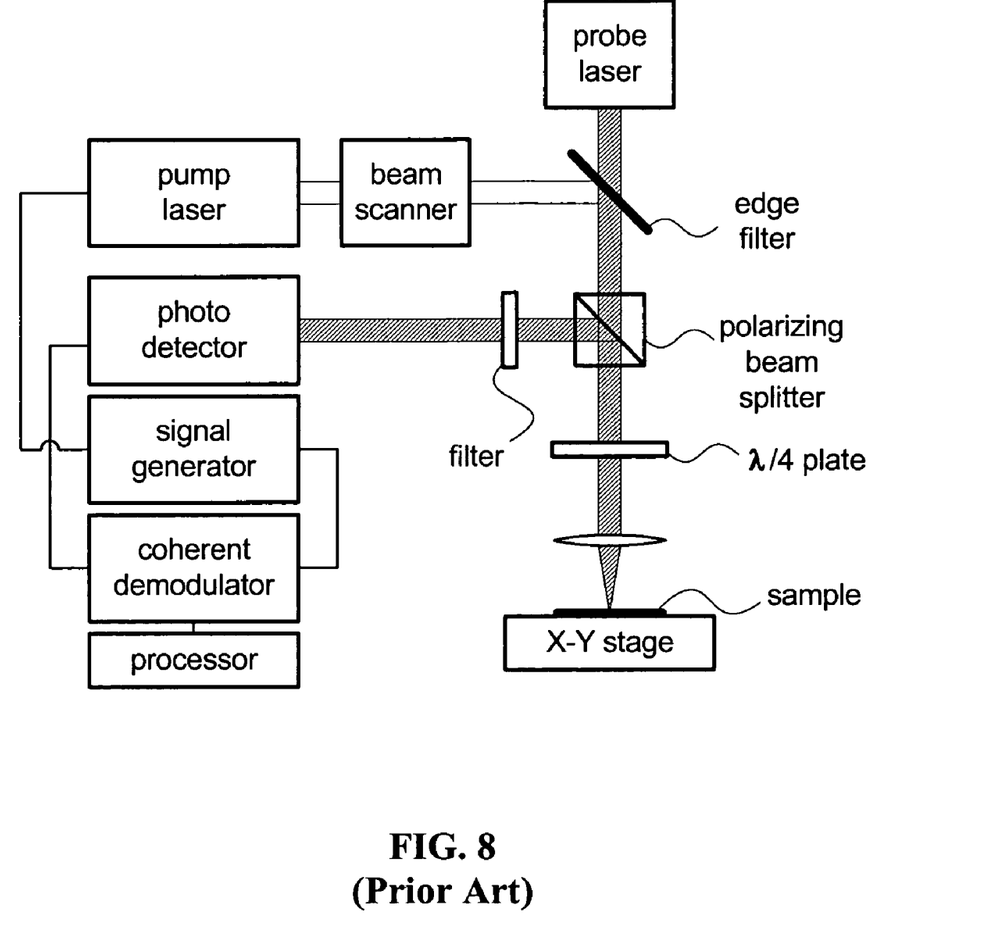
FIG. 8 is a block diagram of a prior art pump and probe beam device.

FIG. 8 shows a basic schematic of a Therma-Probe type tool. Details of such a system are described in the above cited patents. As can be seen, the system 100 includes a pump laser. The output of the pump laser is intensity modulated via the input of a coherent demodulator. The pump laser is focused onto the sample to periodically excite a region thereon to create thermal and plasma waves. The effect of the periodic excitation is monitored with a probe laser. The reflected probe laser beam is directed though a filter to a photodetector. The filter removes pump beam light. The photodetector monitors changes in power of the reflected probe beam caused by changes in optical reflectivity of the sample induced by the periodic excitation. The signals from the detector are analyzed using a heterodyne or lock-in detector which generates separate in-phase (I) and quadrature (Q) outputs. The I and Q outputs are analyzed by the processor.

In conclusion, a method for simultaneously monitoring the peak carrier concentration and USJ junction depth includes a calibration step where the PMR signal from samples with known C and $X_j$ are identified in I-Q space. In a following measuring step, the PMR signal from an unknown sample is measured to obtain Q and I values. The in-phase and quadrature values are then compared, in I-Q space, to the known peak concentration and junction depth to characterize the USJ.

It should be noted that the method of present invention could be calibrated to determine not only the peak carrier concentration but also any desirable parameter of carrier concentration profile and/or any other concentration-related characteristics (area below concentration profile, etc.).

It should also be noted that this measurement method is useful both as described, and as a part of a more complex analysis. It means that they may be cases where this technique will be used in combination with related measurements, for example with the measurements of USJ abruptness and other characteristics of implanted and activated semiconductor wafers.

We claim:

1. A method of determining peak carrier concentration in an ultra shallow junction formed on a semiconductor sample comprising the steps of:
   periodically exciting a region on the surface of the sample;
   directing a probe beam to reflect off the region on the sample being periodically excited;
   monitoring the periodic changes in the reflected probe beam and generating output signals in response thereto;
   analyzing the output signals with a phase synchronous detection system and generating in-phase (I) and quadrature (Q) signals corresponding thereto; and
   comparing the Q and I signals with reference signals to determine the peak carrier concentration of the ultra shallow junction.

2. A method as recited in claim 1, wherein the reference signals are Q and I signals obtained from calibration samples, wherein the calibration samples are also independently measured to determine the peak carrier concentration of the ultra shallow junction.

3. A method as recited in claim 2, wherein the calibration samples are independently measured with a secondary ion mass spectroscopy system.

4. A method as recited in claim 1, wherein said Q and I signals are compared with the reference signals to determine the depth of the junction.

5. A method as recited in claim 1, wherein the periodic changes in the power of the probe beam are monitored.

6. A method of determining peak carrier concentration and junction depth in an ultra shallow junction formed on a semiconductor sample comprising the steps of:
   periodically exciting a region on the surface of the sample;
   directing a probe beam to reflect off the region on the sample being periodically excited;
   monitoring the periodic changes in the reflected probe beam and generating output signals in response thereto;

analyzing the output signals with a phase synchronous detection system and generating in-phase (I) and quadrature (Q) signals corresponding thereto; and comparing the Q and I signals with Q and I reference signals obtained from a set of calibration reference samples to determine the peak carrier concentration and junction depth of the ultra shallow junction.

7. A method as recited in claim 6, wherein the reference signals are Q and I signals obtained from calibration samples, wherein the calibration samples are also independently measured to determine the peak carrier concentration of the ultra shallow junction.

8. A method as recited in claim 7, wherein the calibration samples are independently measured with a secondary ion mass spectroscopy system.

9. A method as recited in claim 6, wherein the periodic changes in the power of the probe beam are monitored.

* * * * *